США009161813B2

United States Patent
Benamou

(10) Patent No.: US 9,161,813 B2
(45) Date of Patent: Oct. 20, 2015

(54) RF ENERGY CONSOLE INCLUDING METHOD FOR VESSEL SEALING

(71) Applicant: Steffan Benamou, Morgan Hill, CA (US)

(72) Inventor: Steffan Benamou, Morgan Hill, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 121 days.

(21) Appl. No.: 13/911,673

(22) Filed: Jun. 6, 2013

(65) Prior Publication Data

US 2014/0025061 A1 Jan. 23, 2014

Related U.S. Application Data

(60) Provisional application No. 61/673,993, filed on Jul. 20, 2012.

(51) Int. Cl.
*A61B 18/12* (2006.01)
*A61B 18/18* (2006.01)
*A61B 18/00* (2006.01)

(52) U.S. Cl.
CPC ............ *A61B 18/18* (2013.01); *A61B 18/1206* (2013.01); *A61B 2018/0063* (2013.01); *A61B 2018/00642* (2013.01); *A61B 2018/00666* (2013.01); *A61B 2018/00678* (2013.01); *A61B 2018/00702* (2013.01); *A61B 2018/00708* (2013.01); *A61B 2018/00827* (2013.01); *A61B 2018/00875* (2013.01); *A61B 2018/00892* (2013.01)

(58) Field of Classification Search
CPC ............ A61B 2018/0063; A61B 2018/00571; A61B 2018/00577; A61B 2018/00636; A61B 2018/00642; A61B 2018/00648; A61B 2018/00666; A61B 2018/0678; A61B 2018/00696; A61B 2018/00672; A61B 2018/00702; A61B 2018/00708; A61B 2018/0072; A61B 2018/00755; A61B 2018/00767; A61B 2018/00827; A61B 2018/00892; A61B 2018/00773
USPC ................................... 606/32–38
See application file for complete search history.

(56) References Cited

U.S. PATENT DOCUMENTS

| 4,191,188 | A | 3/1980 | Belt et al. |
|---|---|---|---|
| 5,472,443 | A | 12/1995 | Cordis et al. |
| 5,540,684 | A | 7/1996 | Hassler, Jr. |
| 5,827,271 | A | 10/1998 | Buysse et al. |
| 6,033,399 | A | 3/2000 | Gines |
| 6,228,080 | B1 | 5/2001 | Gines |
| 6,398,779 | B1 | 6/2002 | Buysse et al. |
| 6,796,981 | B2 | 9/2004 | Wham et al. |
| 6,966,907 | B2 | 11/2005 | Goble |

(Continued)

*Primary Examiner* — Jaymi Della
(74) *Attorney, Agent, or Firm* — Flynn, Thiel, Boutell & Tanis, P.C.

(57) ABSTRACT

A RF energy console controls RF energy output from a RF generator for sealing blood vessels. The energy console includes a processor that executes routines and a controller feedback circuit that, in combination, control the RF generator. Operation includes a heating stage outputting a RF ramping voltage and determining a decrease in measured current to less than a predetermined % percentage of a maximum measured and stored current value to advance to a sealing stage. Then, the voltage is controlled to maintain an increasing change in impedance until a change in current value approaches a flat curve indicating seal completion, which stops the RF generator output. To reseal or enhance a blood vessel seal, the energy console executes the same routines as in the initial sealing operation.

22 Claims, 12 Drawing Sheets

(56) References Cited

U.S. PATENT DOCUMENTS

| | | |
|---|---|---|
| 6,984,231 B2 | 1/2006 | Goble et al. |
| 7,030,623 B1 * | 4/2006 | Carpenter ............... 324/542 |
| 7,090,673 B2 | 8/2006 | Dycus et al. |
| 7,137,980 B2 | 11/2006 | Buysse et al. |
| 7,282,048 B2 | 10/2007 | Goble et al. |
| 7,303,557 B2 | 12/2007 | Wham et al. |
| 7,344,532 B2 | 3/2008 | Goble et al. |
| 7,364,577 B2 | 4/2008 | Wham et al. |
| RE40,338 E | 5/2008 | Biegelsen et al. |
| 7,491,199 B2 | 2/2009 | Goble |
| 7,722,601 B2 | 5/2010 | Wham et al. |
| 7,901,400 B2 | 3/2011 | Wham et al. |
| 7,972,328 B2 | 7/2011 | Wham et al. |
| 7,993,332 B2 | 8/2011 | Goble et al. |
| 8,002,769 B2 | 8/2011 | Goble et al. |
| 8,012,150 B2 | 9/2011 | Wham et al. |
| 8,080,008 B2 | 12/2011 | Wham et al. |
| 8,105,323 B2 | 1/2012 | Buysse et al. |
| 8,147,485 B2 | 4/2012 | Wham et al. |
| 8,216,223 B2 | 7/2012 | Wham et al. |
| 8,267,929 B2 | 9/2012 | Wham et al. |
| 8,287,528 B2 | 10/2012 | Wham et al. |
| 8,298,223 B2 | 10/2012 | Wham et al. |
| 8,303,580 B2 | 11/2012 | Wham et al. |
| 2004/0167508 A1 | 8/2004 | Wham et al. |
| 2007/0173803 A1 | 7/2007 | Wham et al. |
| 2009/0157071 A1 | 6/2009 | Wham et al. |
| 2012/0130256 A1 | 5/2012 | Buysse et al. |
| 2012/0150170 A1 | 6/2012 | Buysse et al. |
| 2012/0283731 A1 | 11/2012 | Unger et al. |
| 2013/0041367 A1 | 2/2013 | Wham et al. |

* cited by examiner

RF ENERGY CONSOLE INCLUDING METHOD FOR VESSEL SEALING

CROSS REFERENCE TO RELATED APPLICATION

This application claims the benefit of U.S. Provisional Application No. 61/673,993, filed Jul. 20, 2012, the disclosure of which is hereby incorporated by reference in its entirety.

FIELD OF THE INVENTION

This invention is related to a RF energy console for outputting RF energy to a handpiece and a method for sealing a blood vessel. The RF energy also can be applied to enhance a seal of a blood vessel that was previously desiccated.

BACKGROUND OF THE INVENTION

The use of an RF generator device in combination with a surgical tool to seal blood vessels is known as disclosed, for example, in U.S. Pat. No. 7,090,673. Further, a bi-polar electrosurgical instrument including a cutting knife in combination with jaw members for sealing and subsequently cutting a blood vessel was known. Various approaches for sealing vessels include RF generator devices that apply RF energy pulses to tissue.

In instances when sealing of a blood vessel is complete, resealing to enhance the seal can be difficult. For heating of fluid in a blood vessel to a boiling condition during a resealing operation, a maximum measured current typically has a much smaller value before boiling begins than a maximum current for a first original sealing operation. Therefore, sealing arrangements that merely compare measured values with a maximum or minimum value for one or more of: current, voltage and impedance, typically are modified by providing different algorithms or calculations for resealing a blood vessel as compared to an initial sealing process.

SUMMARY OF THE INVENTION

In order to obviate or at least minimize the disadvantages of complicated energy applying features of known arrangements, the invention utilizes measured voltage, measured current, changes in current and changes in impedance to control the RF generator to seal a blood vessel. At start-up, a predetermined stored ramping RF voltage is applied to the jaws of a handpiece during a heating stage to obtain boiling of liquid in tissue and in a blood vessel. During heating, current is measured and when a current drop or decrease of a certain predetermined percent value occurs, the sealing operation advances from the heating stage to a sealing stage. During the sealing stage the invention relies on a flattening of a change in current curve to accurately determine completion of a seal.

By utilizing a percent decrease in current value to determine boiling of liquid, resealing a blood vessel can occur without requiring different routines, algorithms or comparison values as compared to an initial sealing.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which.

DETAILED DESCRIPTION OF THE INVENTION

A RF energy console 10 and a method for sealing blood vessels and resealing blood vessels during a medical procedure is described. Note that in this description, references to "one embodiment" or "an embodiment" mean that the feature being referred to is included in at least one embodiment of the present invention. Further, separate references to "one embodiment" or "an embodiment" in this description do not necessarily refer to the same embodiment; however, such embodiments are also not mutually exclusive unless so stated, and except as will be readily apparent to those skilled in the art from the description. For example, a feature, step, etc. described in one embodiment may also be included in other embodiments. Thus, the present invention can include a variety of combinations and/or integrations of the embodiments described herein.

Figure 1:
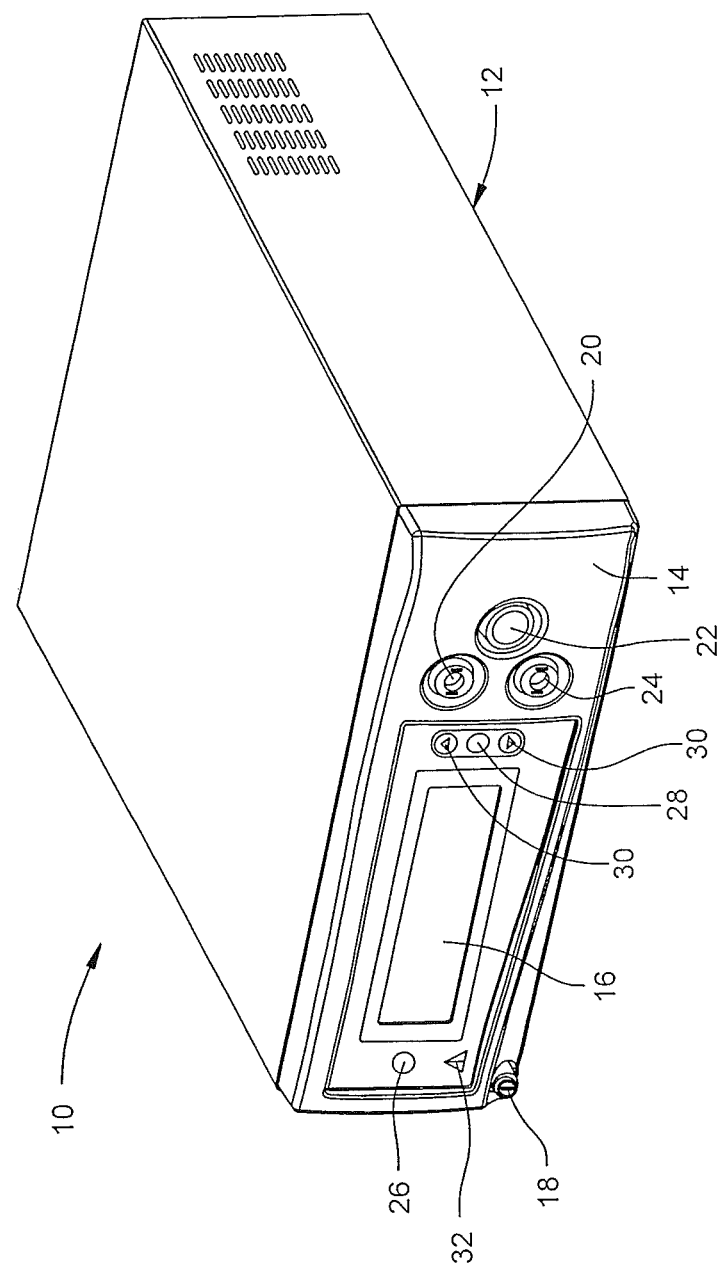
FIG. 1 shows an exterior view of a RF energy console.

FIG. 1 shows a RF energy console 10 according to certain embodiments of the invention. The RF energy console 10 has a housing 12 including a front face panel 14. The front face panel 14 includes a display screen 16, an on/off control 18 to power on the RF energy console 10, an RF energy output connector port 20 and a powered shaver output connector port 22. A foot switch connector port 24 is also provided on the front face panel 14. Adjacent the display screen 16, the directed energy console 10 includes an output device selector 28 and device adjustment controls 30 that are disposed vertically above and below the output device selector. An RF vessel seal error indicator 32 is disposed on the front face panel 14. A specific error indication can be provided on the display screen 16. Further, a progress bar provided on the display screen 16 indicates progress and completion of a seal.

Figure 2:
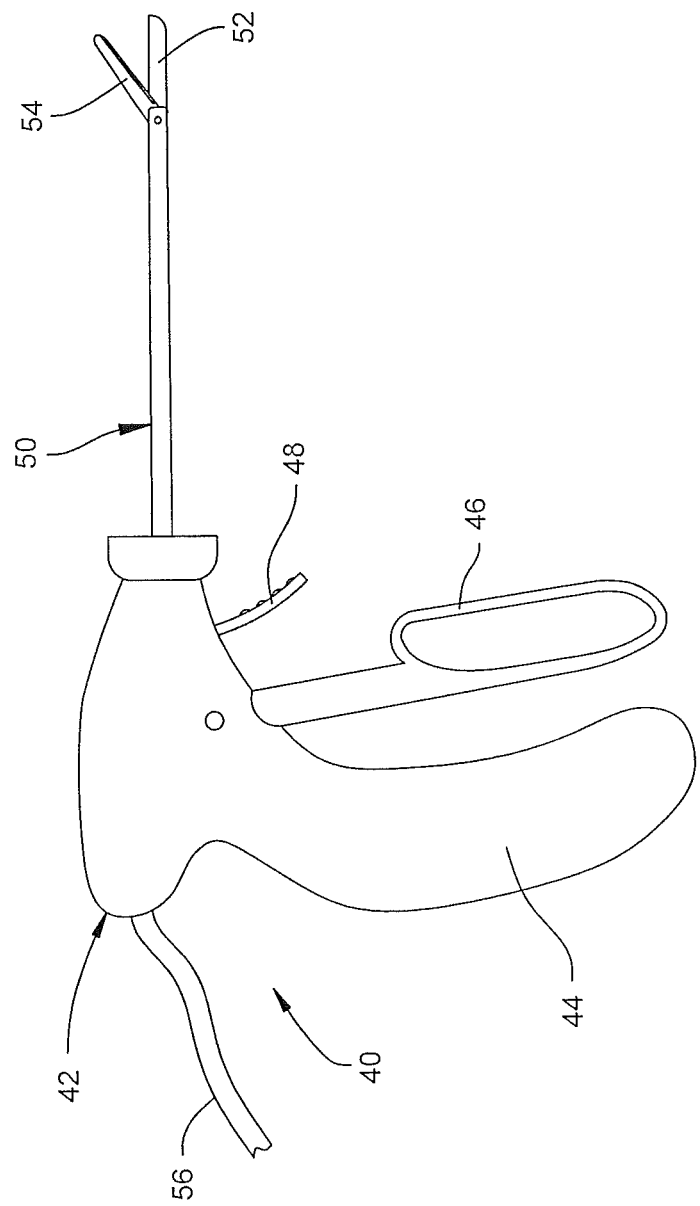
FIG. 2 shows an exterior view of a handpiece for sealing blood vessels.

FIG. 2 shows an electrosurgical handpiece 40 for receiving energy from the RF energy console 10. The handpiece 40 includes a handpiece body 42 having a fixed handle 44. In the FIG. 2 embodiment, the handpiece 40 supports a movable handle 46 and a pivotable cutting device trigger 48. A shaft apparatus 50 has a proximal end secured to a front end of the handpiece body 42. The shaft apparatus 50 includes a fixed jaw 52 and a movable jaw 54 each disposed at a distal end thereof. Force applied to the movable handle 46 clamps a blood vessel between the jaws 52, 54. Actuating the cutting device trigger 48 moves a cutting blade (not shown) outwardly along the longitudinal axis of the shaft apparatus 50 to cut tissue of a sealed blood vessel disposed between the jaws 52, 54.

A foot switch or foot pedal (not shown) can be plugged into the foot switch connector port 24 to provide an actuation signal to the RF energy console 10 to apply energy to the handpiece 40 for sealing a blood vessel. In some embodiments, an actuation switch (not shown) disposed on the handpiece body 42 is provided to trigger operation of the RF energy console 10 for sealing a blood vessel.

Cable 56 illustrated in FIG. 2 protrudes from the surgical handpiece 40 for connection to RF energy output connector port 20 of the RF energy console 10.

Figure 3:
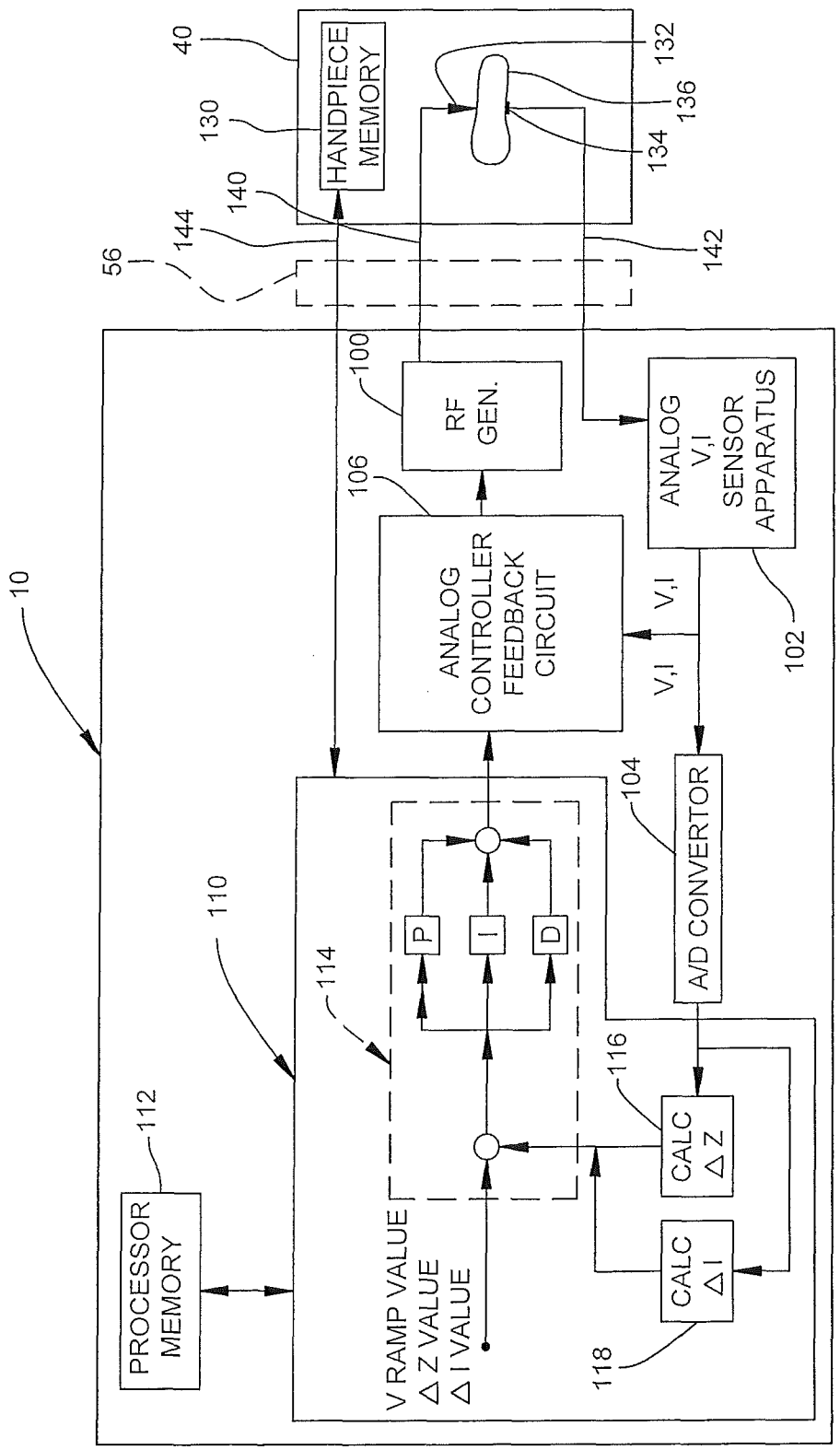
FIG. 3 is a block diagram of the RF energy console and the handpiece.

FIG. 3 is a block diagram of the RF energy console 10, the handpiece 40 and the cable 56 providing a connection therebetween. The embodiment shown in FIG. 3 includes a RF generator 100 and an analog voltage/current (V/I) sensor apparatus 102 disposed in the housing 12 of the RF energy console 10. The analog sensor apparatus 102 is connected to an analog to digital (A/D) converter 104 and to an analog controller feedback circuit 106. The A/D converter connects to a digital processor 110 also disposed within the RF energy console 10 that is provided with a processor memory 112. FIG. 3 shows the digital processor 110 including a feedback circuit representation 114, a change in impedance calculator representation 116, and a change in current calculator representation 118. The representations are of calculations or actions that are performed by the digital processor 110.

Further, in some embodiments, one or more of a predetermined stored start-up increasing voltage ramping value for a heating stage, a predetermined stored ramp voltage limit value, a predetermined stored ramp current limit value, a predetermined stored current decrease percentage threshold value (defined by the constant "$\%_{th}$" and having a possible value between 1 and 99), a predetermined stored change in impedance value ($\Delta Z_{seal}$) for use during a sealing stage, and a predetermined stored change in current shut-off value ($\Delta I_{shutoff}$) for use during a sealing stage can be stored in a handpiece memory 130 illustrated in FIG. 3 and read by the digital processor 110.

The block diagram of the handpiece 40 shown in FIG. 3 includes a drive electrode/jaw representation 132 corresponding to movable jaw 54 and a ground electrode/jaw representation 134 corresponding to jaw 52 that encompass a tissue/blood vessel representation 136 disposed therebetween.

Cable 56 as shown in FIG. 3 connects the handpiece 40 to the RF energy console 10 via the RF output connector port 20. The cable 56 includes a RF output connector 140 that provides RF energy from the RF generator 100 to the drive electrode/jaw representation 132. Likewise, the cable 56 includes an RF return/ground connector 142 that connects the ground electrode/jaw representation 134 through the RF output connector port 20 to the analog sensor apparatus 102. A 1-wire connector 144 connects the surgical handpiece memory 130, typically a non-volatile random access memory (NVRAM), through the connector port 20 to the digital processor 110 disposed within the RF energy console 10. The connectors 140, 142 typically extend essentially the length of the shaft apparatus 50 and through the handpiece body 42 to the cable 56. The handpiece memory 130 can be located within the handpiece body 42 adjacent the cable 56. The 1-wire connector 144 for the handpiece memory 130 typically is located within the body or shell of the cable 56 at the end that connects to the RF energy output connector port 20.

The predetermined start-up increasing voltage ramping value, the predetermined ramp voltage limit value, the predetermined ramp current limit value, the current decrease $\%_{th}$ threshold value, the $\Delta I_{shutoff}$ value, the $\Delta Z_{seal}$ value and other values, along with a handpiece identifier unique to the particular handpiece 40 can be obtained from the surgical handpiece memory 130 and stored in the digital processor memory 112.

In another embodiment, only a surgical handpiece identifier is stored in the surgical handpiece memory 130. In this embodiment, the digital processor 110 reads the handpiece identifier from the handpiece memory 130 and locates the specific predetermined stored values for the identified surgical handpiece 40 in a remote memory device accessible over a network or similar arrangement. In another embodiment the specific values are pre-stored in the processor memory 112, instead of the handpiece memory.

The predetermined stored values typically also include one or more predetermined error time limit values that, for example, discontinue RF output from the RF generator 100 when a change in the first heating stage 1 or the second sealing stage 2 does not occur within a predetermined time limit. The predetermined stored time limit values can be obtained by the processor 110 in the various ways that the predetermined stored values are obtained as discussed above.

In another embodiment, the predetermined stored values additionally include a predetermined stored and instantaneous short circuit current value that is stored in the handpiece memory 130 or elsewhere as in the embodiments discussed above. The processor 110 obtains the short circuit current value and discontinues the output of energy from the RF generator 100 when an instantaneous measured current value exceeds the instantaneous short circuit current value.

In another embodiment, P-I-D values are stored in the handpiece memory 130 and are read by the processor 110. The processor 110 applies the P-I-D values to operate in part as a software based P-I-D controller.

During use of the RF energy console 10 shown in FIGS. 1-3, the RF generator 100 outputs RF energy to the handpiece 40. Energy output from the movable jaw 54 passes through tissue that includes a blood vessel 136 and is received at the fixed jaw 52. Connector 142 provides an electrical return path from the fixed jaw 52 through the cable 56 to the RF energy console 10.

In another embodiment, the fixed jaw 52 receives RF energy and the energy received by the fixed jaw 52 passes through tissue to the movable jaw 54. In this embodiment, the movable jaw 54 is connected to the RF energy console 10 via connector 142, and the fixed jaw 52 connects to the RF generator 100 via the connector 140 and the cable 56.

As shown in FIG. 3, after passing through tissue 136, energy is received at ground electrode/jaw representation 134 and provided to the analog V, I sensor apparatus 102 via connector 142. The analog sensor apparatus 102 determines RMS voltage and current values for the RF energy output by the RF generator 100 and returned to jaw 52. The measured RMS voltage and current values are provided to the analog controller feedback circuit 106, as well as to an A/D converter 104. The A/D converter 104 converts the analog measured current and voltage values to digital values that are provided to the digital processor 110.

The digital processor 110 functions to control RF energy output from the RF generator 100 by providing a control signal to the analog controller feedback circuit 106. The controller feedback circuit 106 operates orders of magnitude faster than the P-I-D software routine and other processing executed by the processor 110. Thus, the analog controller feedback circuit 106, in response to the digital processor control signal, along with measured voltage ($V_{meas}$) and/or measured current ($I_{meas}$) values received from the analog sensor apparatus 102, controls the RF generator 100 to output RF energy for sealing a blood vessel.

More specifically, the feedback circuit representation 114 of the digital processor 110 represents software that functions as a P-I-D controller and other circuitry that adjust the output to the RF generator 100 to prevent or minimize drastic erroneous changes in the RF energy output to the handpiece 40. Further, the digital processor 110 receives the $V_{meas}$ and $I_{meas}$ values through the A/D converter and executes algorithms or routines that act as a comparator to output the proper values from the RF generator 100 and as a feedback circuit to stabilize the processor control signal provided from the digital processor 110 to the analog controller feedback circuit 106 to assist in controlling and stabilizing the output of the RF generator 100.

OPERATION

In one embodiment, upon powering up of the RF energy console 10, the digital processor 110 operates as follows. Initially, the digital processor 110 receives a handpiece identifier via connector 144 from a memory 130 of a handpiece 40 when a handpiece cable 56 is secured to the RF energy output port 20. From the handpiece memory 130, the digital processor 110 receives information to determine the specific type and model of the handpiece 40 and that the handpiece is intended for sealing blood vessels. Moreover, the digital processor 110 obtains the predetermined stored start-up increasing voltage ramping value, the predetermined stored ramp voltage limit value, the predetermined stored ramp current limit value, the $\%_{th}$ value, the $\Delta I_{shutoff}$ value, the $\Delta Z_{seal}$ value and one or more of the additional values discussed above, as necessary. The predetermined stored values correspond to the specific handpiece 40 and enable a RF energy output that efficiently seals a blood vessel.

Figure 4:
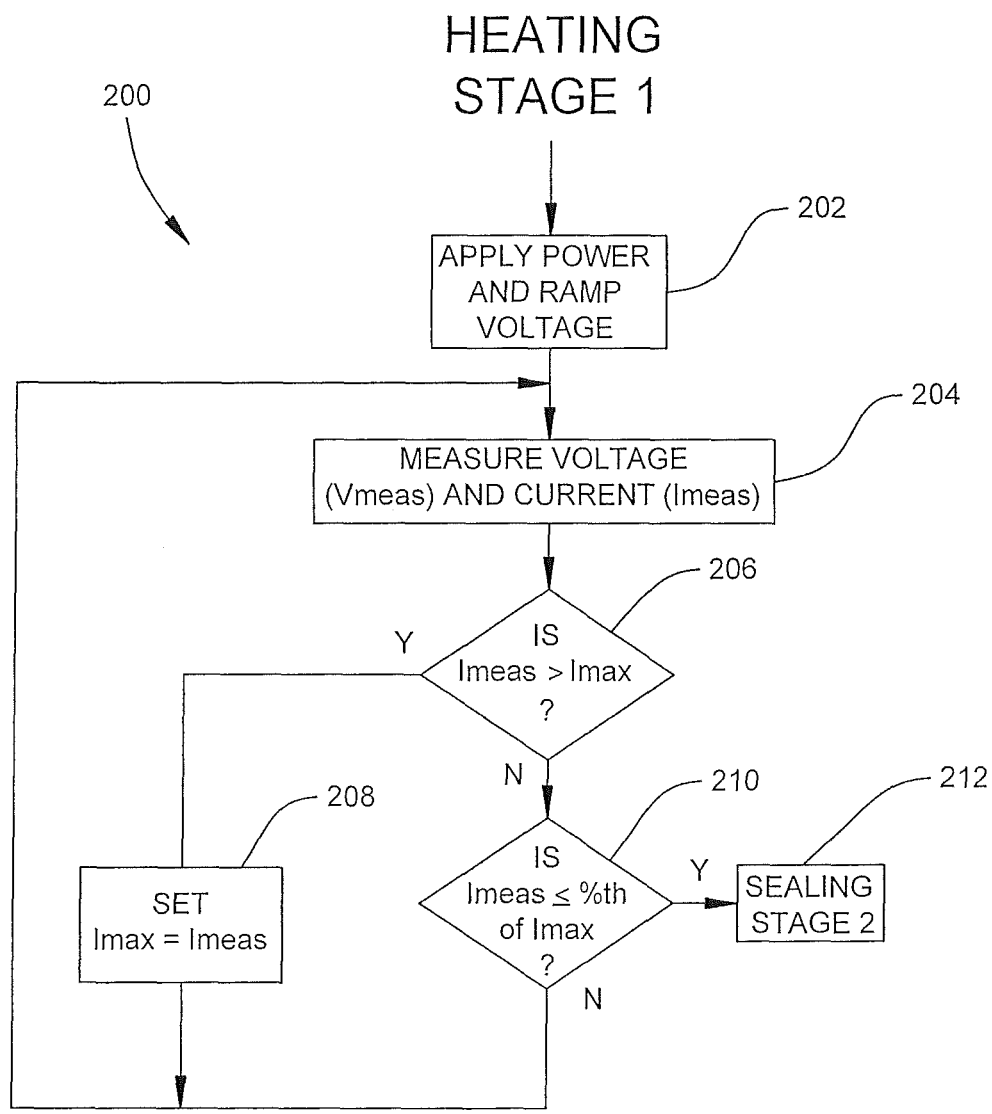
FIG. 4 shows a flow chart of a first heating stage of the RF energy console.
Figure 5:
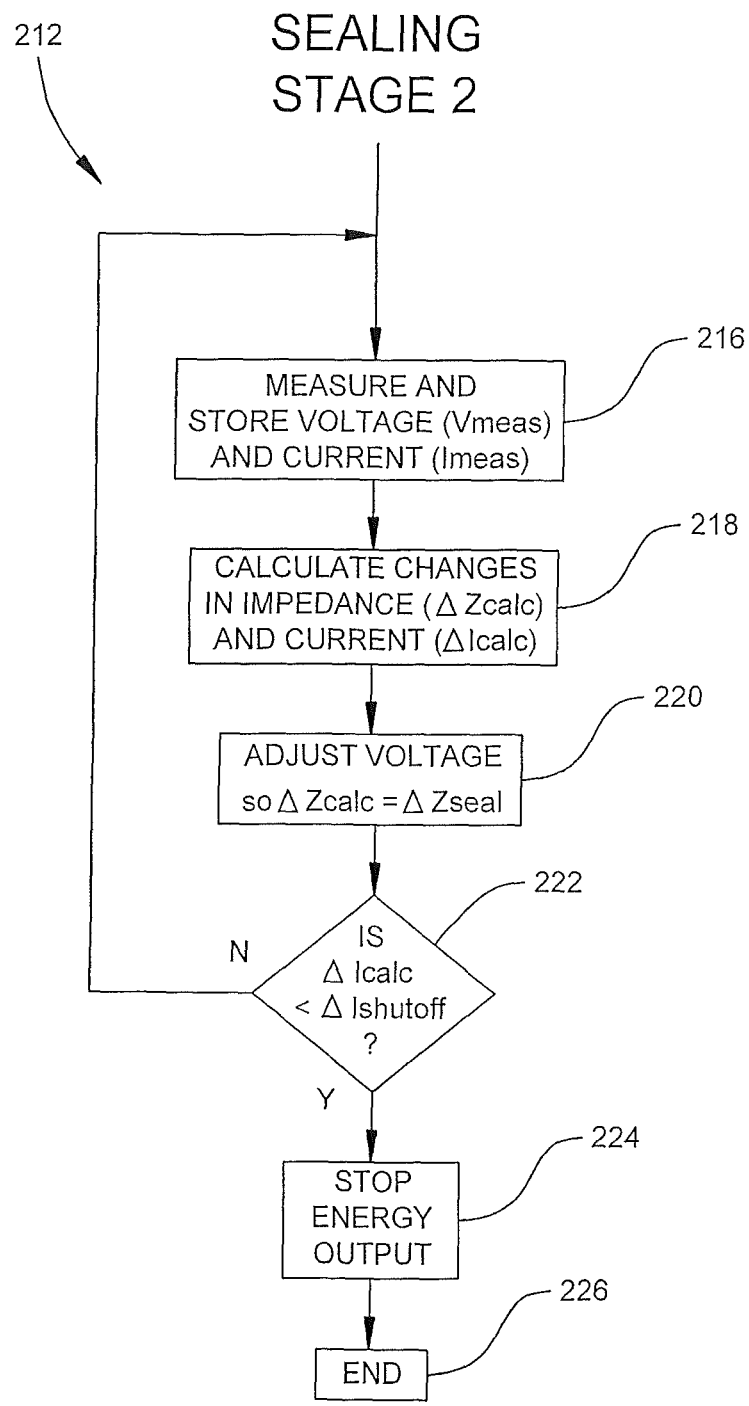
FIG. 5 shows a flow chart that illustrates a second sealing stage for sealing a blood vessel.

In one embodiment, the RF energy device console 10 operates as shown in the flow charts of FIGS. 4 and 5. The RF energy console applies the routines 200, 212 to a specific handpiece 40 which results in the measured values shown in the graphs of FIGS. 6-9.

Figure 6:
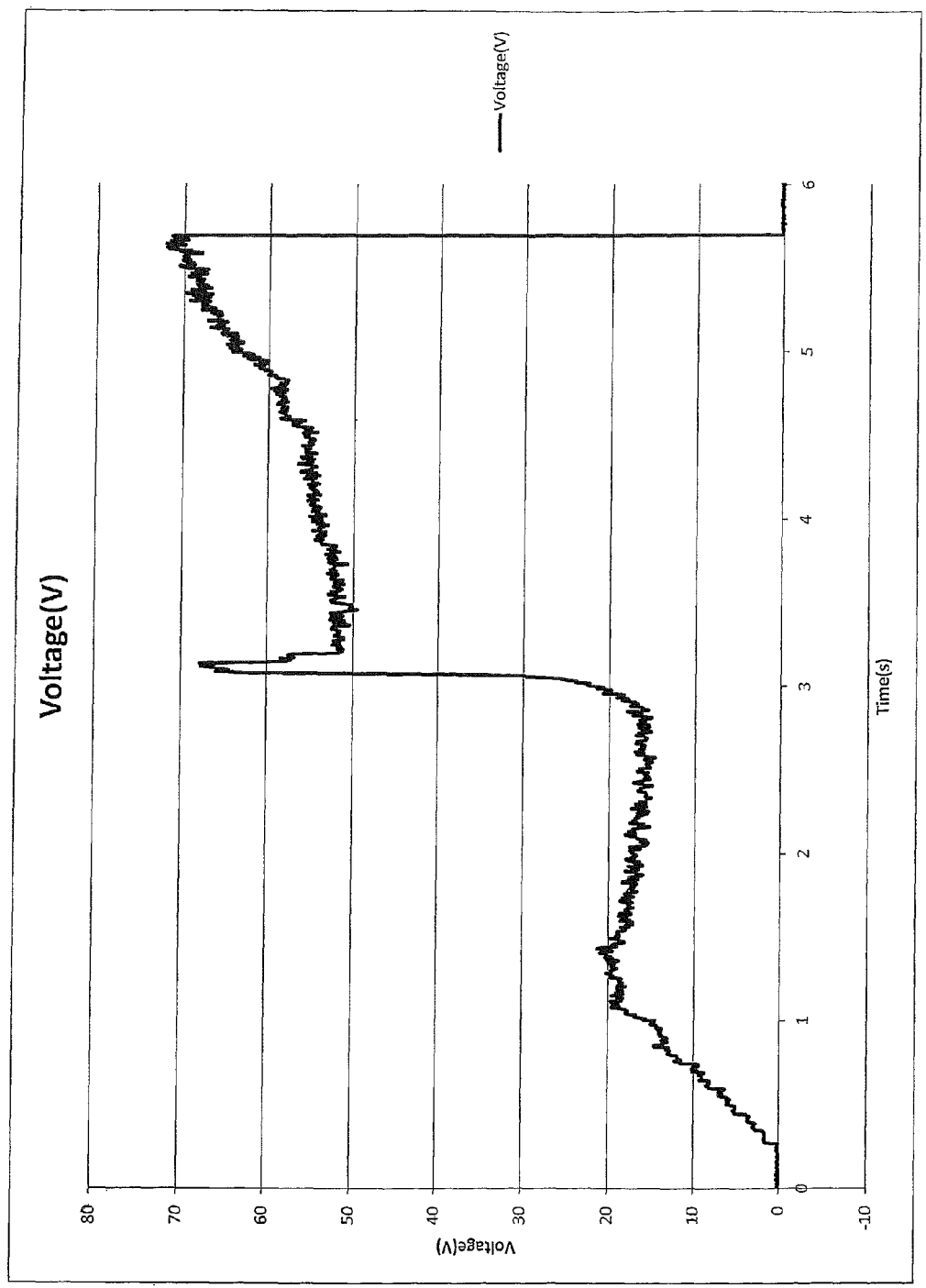
FIG. 6 is a graph of voltage that is output from the handpiece for one blood vessel sealing embodiment.

Upon manual actuation of the RF energy console 10 by a user using a foot pedal or handpiece mounted trigger, during a first heating stage at step 214 shown in FIG. 4, the digital processor 110 outputs a control signal to the controller feedback circuit 106 that begins operation of the RF generator 100 at the start-up increasing voltage ramping value. Thereafter, the processor 110 recalculates the output signal that controls the controller feedback circuit 106 to control the RF generator 100 to ramp the voltage value applied to the blood vessel including tissue 136 via the jaws 52, 54 at an essentially constant increasing rate in accordance with the specific predetermined stored voltage ramping value. The voltage graph of FIG. 6 shows the ramping voltage value beginning at 0 volts at start-up and advancing to 20 volts in slightly more than one second. The ramping voltage is intended to increase at a constant rate, and in some embodiments increases at a value in a range from about 10 volts/second to about 100 volts/second. Start-up of the RF generator 100 occurs after about 0.3 seconds in the embodiment shown in FIGS. 6-9, as no voltage or current is output by the RF generator 100 during the first about 0.3 seconds.

Figure 7:
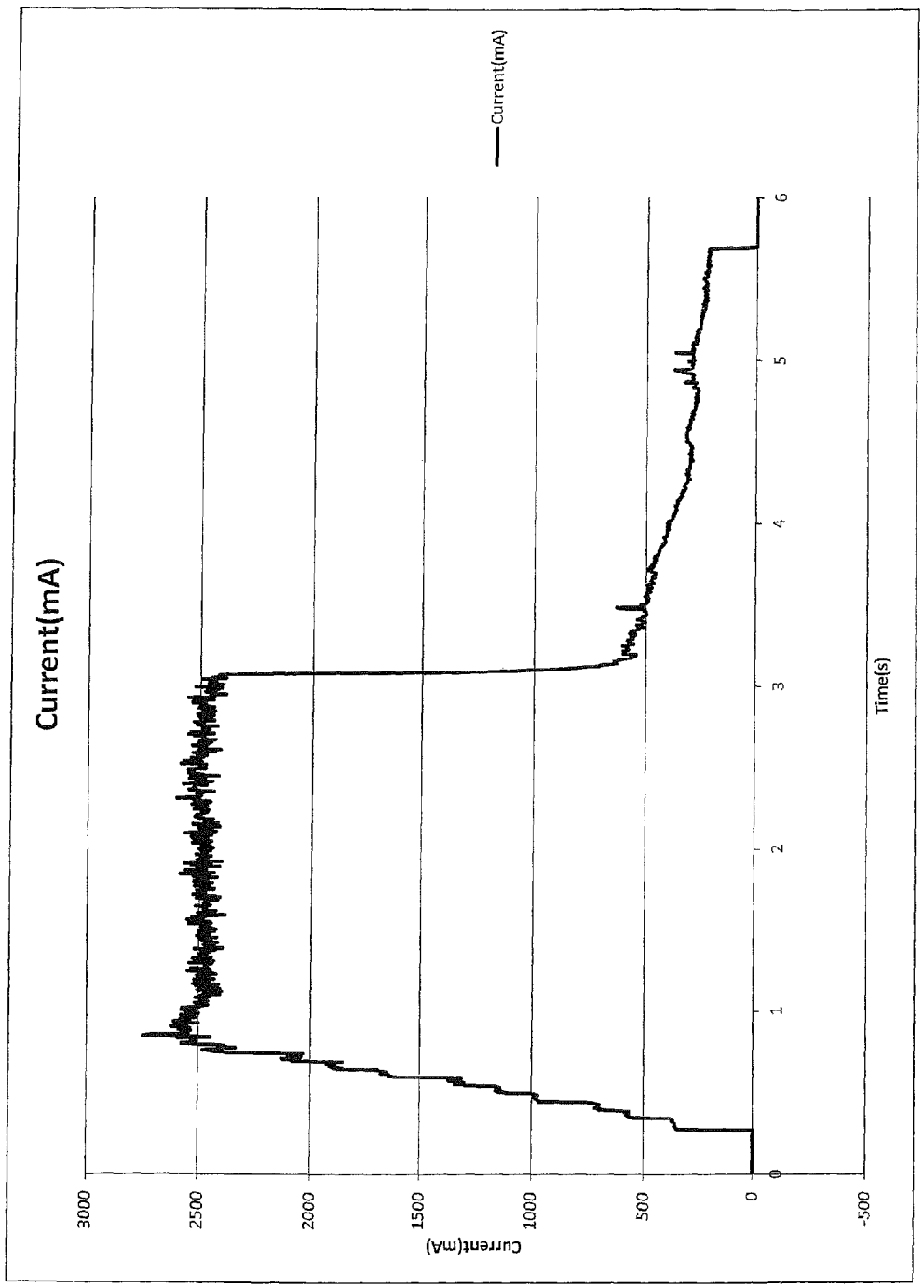
FIG. 7 is a graph of measured current for the embodiment shown in FIG. 6.

When one of a ramp current limit value or a ramp voltage limit value is obtained by the RF generator output, the processor 110 prevents the $V_{meas}$ voltage or $I_{meas}$ current from increasing beyond the respective current or voltage limit value during the heating stage. The ramp voltage limit value is approximately 60 volts for the particular handpiece 40 of the embodiment shown in FIGS. 6-9. The ramp current limit value is about 2,500 milliamps (mA). In FIG. 7, the $I_{meas}$ current is then maintained at about 2,500 mA during the heating stage. Heating stage 1 continues for about 2.7 seconds to about 2.9 seconds in the embodiment shown in FIGS. 6-9.

In some embodiments, the ramp voltage limit value is a single value within a range from about 30 volts to about 100 volts, and preferably within a range from about 60 volts to about 70 volts. The ramp voltage limit value depends on the size of a blood vessel, type of tissue, properties of the handpiece 40 and other factors. These types of factors affect which of the ramp voltage limit value or the ramp current limit value is first obtained for controlling the voltage output during the heating stage of the sealing operation. In some embodiments, the ramp current limit value is a single value within a range of about 1000 mA to about 5000 mA. The measurements of $V_{meas}$ voltage and $I_{meas}$ current occur during step 202 as shown in FIG. 4 until the ramp current limit value or the ramp voltage limit value is obtained and thereafter occur while the limit value is maintained.

As shown in FIG. 4 at step 204, the analog voltage/current sensor apparatus 102 measures the $V_{meas}$ voltage value and the $I_{meas}$ current value. Besides the digital processor 110 maintaining or attempting to maintain the $V_{meas}$ voltage value at a value that is less than the predetermined ramp voltage limit value, the digital processor also maintains the $I_{meas}$ current value below the predetermined ramp current limit value, such as 2,500 mA. The $V_{meas}$ voltage value and the $I_{meas}$ current value are provided to the feedback circuit 106. The feedback circuit 106 and the digital processor 110 account for changes in current, voltage and other factors to maintain the $V_{meas}$ voltage value at or below the predetermined ramp voltage limit value and the $I_{meas}$ current value at or below the ramp current limit value.

Initially increasing the $V_{meas}$ voltage value over the first heating stage as shown in FIG. 6, and thereafter while maintaining the ramp current limit value of 2,500 mA, the digital processor 110 also compares the $I_{meas}$ current value to a maximum ($I_{max}$) RMS current value for heating stage 1 as shown at step 206 in FIG. 4. Typically, the $I_{max}$ current value at start-up is a relatively low current value and the $I_{meas}$ current value output by the RF generator 100 increases as shown in FIG. 7 as the voltage ramping value increases. If the ramp voltage limit value is obtained first, the $I_{meas}$ current value is at a value less than the ramp current limit value. In FIG. 7, the $I_{meas}$ current value is essentially 0 mA at start-up and is about 2500 mA when the ramp current limit voltage value is obtained. Regardless of whether the $I_{meas}$ current value attains the current limit value in less than a second, when the $I_{meas}$ current value is greater than the stored $I_{max}$ current value, the routine or algorithm 200 shown in FIG. 4 advances to step 208. At step 208, the $I_{max}$ current value stored in the digital processor memory 112 is updated to the greater $I_{meas}$ current value and the routine 200 returns to step 204 and repeats determining a $V_{meas}$ voltage value and an $I_{meas}$ current value. Thus, the $I_{max}$ current value stored by the processor 110 is eventually updated to a value of about 2500 mA for the embodiment of FIGS. 6-9. As discussed above, the digital processor 110 and the analog controller feedback circuit 106 operate to ensure that the $I_{meas}$ current value does not exceed the ramp current limit value and that the $V_{meas}$ voltage value output by the RF generator 100 does not exceed the predetermined ramp voltage limit value.

At step 206, when the $I_{meas}$ current value is less than or equal to the $I_{max}$ current value, the routine 200 advances to step 210. At step 210, the digital processor 110 compares the $I_{meas}$ current value to the predetermined stored current decrease threshold %$_{th}$ of the I$_{max}$ current value. The %$_{th}$ value is dependent on the type of handpiece 40 being utilized. For example, the %$_{th}$ value can be a single value in a range between about 20% and about 95%, in a range between about 60% and about 90% or in a specific range between about 70% and about 85%. Before fluid in tissue of a blood vessel begins to boil, the I$_{meas}$ current value typically increases during the start up heating stage for less than one second of operation and does not decrease significantly as shown in the graph of FIG. 7 for more than the next two seconds of operation. Thus, for the embodiment shown in FIGS. 6-9, the routine 200 continues to return to step 204 and repeats for more than two seconds of operation.

Eventually, the fluid in the tissue and in the blood vessel between the jaws 52, 54 begins boiling causing tissue impedance to increase and current to decrease, and thus the I$_{meas}$ current value suddenly decreases a large amount. FIG. 7 shows the measured current decreasing from about 2500 mA to almost about 500 mA in a small number of milliseconds, which is about a 80% decrease in the I$_{meas}$ current value. Thus, the I$_{meas}$ current value suddenly becomes less than or equal to %$_{th}$ of the I$_{max}$ current value which signifies boiling, so long as the %$_{th}$ value is greater than about 20%. Then, the routine 200 advances from step 210 to the sealing stage 2 illustrated by the sealing routine 212 shown in FIG. 5. In the embodiment shown in FIGS. 6-9, the sealing stage 2 begins about 2.7 seconds to about 2.9 seconds after the RF generator 100 starts outputting RF energy and continues for about 2.6 to about 2.8 additional seconds before stopping, which results in a total operating time of about 5.5 seconds to complete a seal.

In the sealing routine 212 shown in FIG. 5, the start-up voltage ramping value, and other values used during the heating stage 1 are no longer utilized.

The sealing routine 212 begins at step 216, whereat the V$_{meas}$ voltage value and the I$_{meas}$ current value are obtained. The routine 212 advances from step 216 to step 218 wherein the processor 110 uses the I$_{meas}$ current value and one or more previously stored I$_{meas}$ current values to calculate a change in current ($\Delta$I$_{calc}$) value for the energy output by the RF generator 100 and provided through the jaws 52, 54 to apply to tissue at a blood vessel. More specifically, the $\Delta$I$_{calc}$ value is calculated from changes in I$_{meas}$ current values over a certain time resulting in a $\Delta$I$_{calc}$ value that is measured in mA/second. The V$_{meas}$ voltage value is compared with one or more previously stored V$_{meas}$ voltage values to calculate a change in voltage ($\Delta$V$_{calc}$) that is measured in volts/second. In one embodiment, at each measurement of V$_{meas}$ and I$_{meas}$, an impedance value is calculated. An impedance value is compared with or more previously stored impedance values to calculate a change in impedance ($\Delta$Z$_{calc}$) value that is measured in ohms/second. In another embodiment, $\Delta$Z$_{calc}$ is determined by dividing an essentially real-time $\Delta$V$_{calc}$ value by an essentially real-time $\Delta$I$_{calc}$ value. After performing the calculations at step 218, the routine 212 advances to step 220.

Figure 8:
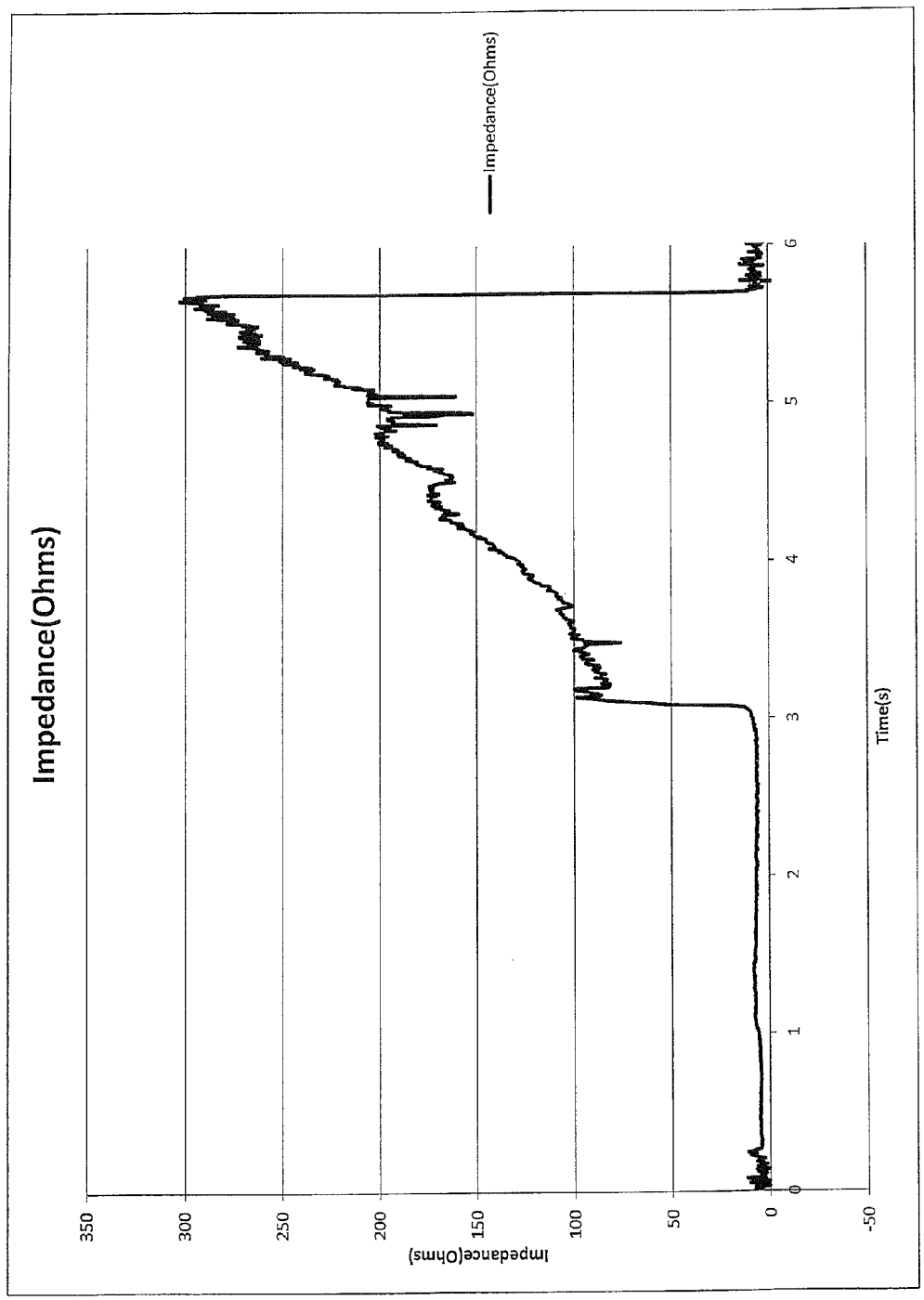
FIG. 8 is a graph showing measured impedance for the embodiment shown in FIG. 6.

At step 220 shown in FIG. 5, the digital processor 110 compares the $\Delta$Z$_{calc}$ value with the predetermined stored positive change in impedance $\Delta$Z$_{seal}$ value for the specific handpiece 40. In some embodiments, the $\Delta$Z$_{seal}$ value is a value with a range of about 25 ohms/second to about 200 ohms/second. In view of the comparison results, the processor 110 in combination with the controller feedback circuit 106, adjusts the voltage value output by the RF generator 100 to maintain the increasing $\Delta$Z$_{seal}$ value for the current path between the jaws 52, 54 and through the tissue including a blood vessel. The increasing linear impedance as measured is shown in FIG. 8, wherein impedance begins to increase after about 2.7 to 2.8 seconds from the start of the sealing operation and continues until the seal is complete. The $\Delta$Z$_{seal}$ value is selected for a handpiece 40 in order to maximize the sealing quality for the blood vessel receiving RF energy from the handpiece. Thus, the purpose of the $\Delta$Z$_{seal}$ value used during the sealing stage is to gradually dessicate the tissue and vessel at a controlled rate slow enough to ensure a quality seal by minimizing charring, but fast enough so the procedure time length is minimized. After the voltage adjustment at step 220, the routine 212 advances to step 222.

During the sealing operation routine 212 shown in FIG. 5, the repeatedly calculated $\Delta$I$_{calc}$ values are negative values as the current is decreasing during the sealing stage 2 which starts at about 3.1 seconds, which is about 2.8 seconds after the RF generator 100 is energized and continues for about 2.5 to 2.6 seconds more as shown in FIG. 7. At step 222, the value is compared to the predetermined stored change in current $\Delta$I$_{shutoff}$ value for the sealing stage. As shown in FIG. 7, after blood vessel sealing nears completion, the I$_{meas}$ current value begins to plateau at a I$_{meas}$ current value of about 250 mA and the change in current begins to flatten toward a change in current of 0 mA/sec. So long as the $\Delta$I$_{calc}$ value is decreasing at a large enough rate, in one embodiment the $\Delta$I$_{shutoff}$ value is −50 mA/second, the routine 212 returns to step 216 and continues to perform steps 216, 218, 220, 222. In some embodiments, the $\Delta$I$_{shutoff}$ value has a value within a range of about −20 mA/second to about −80 mA/second.

At step 222, when the absolute value of the $\Delta$I$_{calc}$ value is less than absolute value of the $\Delta$I$_{seal}$ value, for example a $\Delta$I$_{calc}$ value of −45 mA/second for comparison with a $\Delta$I$_{seal}$ value of −50 mA/second, the routine 212 advances from step 222 to step 224.

At step 224, the digital processor 110 stops the output of energy from the RF generator 100. Further, in some embodiments, a progress bar displayed on the display screen 16 provides a visual indication that the seal is complete. The progress bar shows the advancement of the sealing operation and relies on $\Delta$I$_{calc}$ to do so during the sealing stage. In some embodiments, an audible indication of seal completion is provided.

Figure 9:
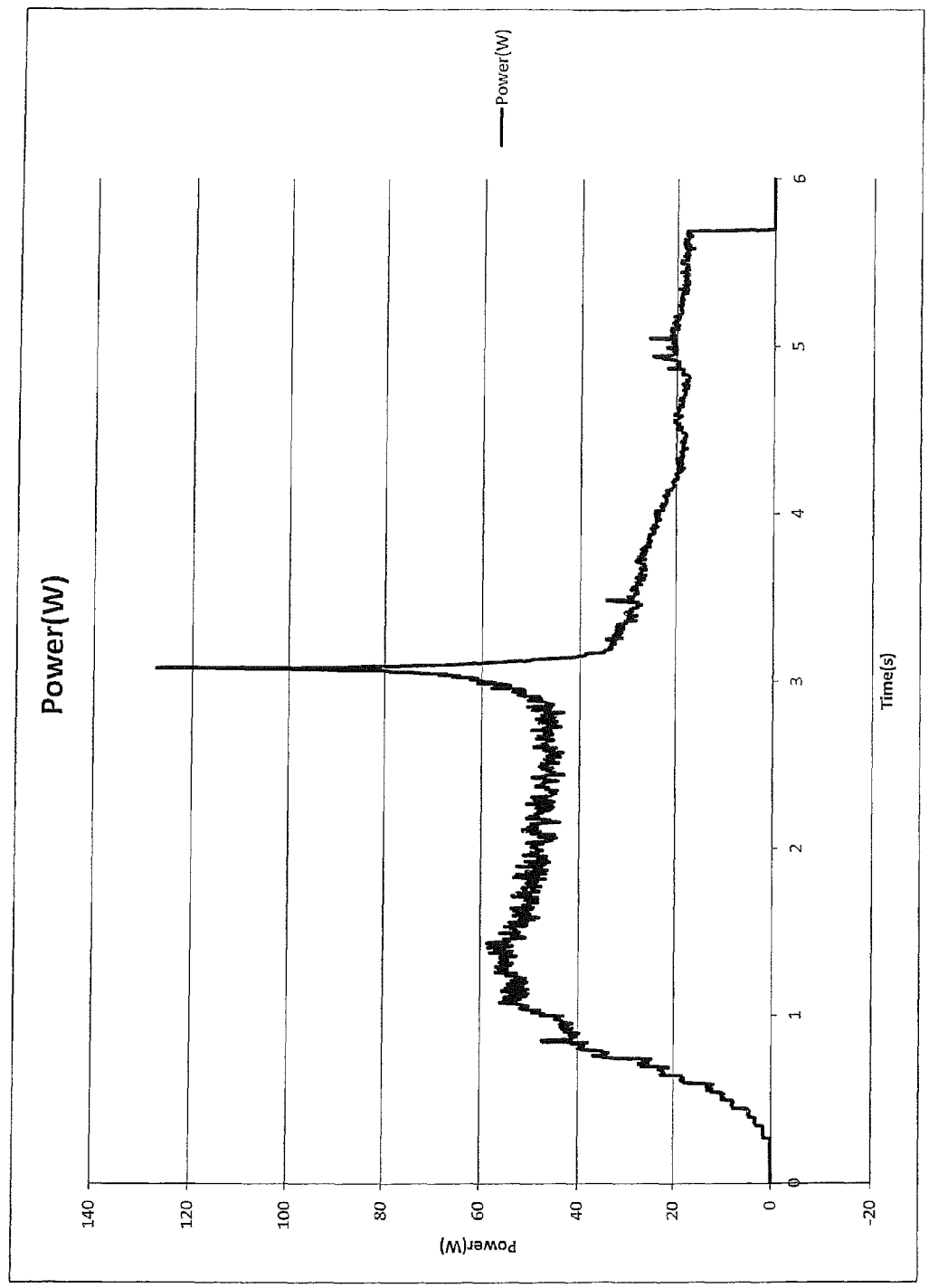
FIG. 9 is a graph displaying power for the embodiment shown in FIGS. 6-8.

FIG. 9 is provided to illustrate power output during heating and sealing stages of the embodiment illustrated in FIGS. 6-8.

INCOMPLETE SEAL

While FIGS. 4 and 5 illustrate a method for completing a sealing operation, the digital processor 110 is capable of performing additional operations during the routines 200, 212, such as stopping the output of energy from the RF generator 100 and providing an indication if the applied RF energy does not result in a proper blood vessel seal.

During the routine 200 shown in FIG. 4, the digital processor 110 essentially simultaneously executes a timing routine that essentially continuously or periodically measures in real-time, the exact time of the heating stage 1 operation and compares the measured time with a predetermined stored heating error time limit value corresponding to the particular handpiece 40 connected thereto. In an instance wherein the I$_{meas}$ current value does not become less than %$_{th}$ of the I$_{max}$ current value (sealing beginning) within the predetermined stored heating error time limit value during the heating stage, the RF output seal error indicator 32 provides a visual indication of sealing failure and RF energy output from the RF generator 100 is discontinued. An audible error message or alarm is provided in some embodiments and a detailed error message is provided on the display screen 16. In some embodiments, the heating error time limit value for the heating stage is a value with a range from about 2 seconds to about 6 seconds.

During the sealing stage 2 operation as illustrated by the routine 212 shown in FIG. 5, the digital processor 110 also continues to measure the time length since the beginning of the sealing operation. In one embodiment, if the measured time exceeds a predetermined stored sealing error time limit value that is stored in the processor memory 112, the seal error indicator 32 provides a visual seal error indication and the RF energy that is output by the RF generator 100 is discontinued. In some embodiments, an audible error message or another alarm is provided and a specific error message can be provided on the display screen 16. In various embodiments, the sealing error time limit value is from about 5 seconds to about 12 seconds from the beginning of a sealing operation, which includes the heating stage.

In some embodiments, a predetermined instantaneous short circuit current value stored in the handpiece memory 130 is sent to the digital processor 110 and then provided to a separate analog circuit (not shown) that determines a sudden rise in instantaneous current beyond the short circuit current value. If the instantaneous measured current value (not a RMS value) is greater than the short circuit current value, the RF energy output from the RF generator is stopped and the seal error indicator 32 provides a visual indication of sealing failure. Likewise, in some embodiments a specific short circuit error message is provided on the display screen 16 and/or an audible message.

RESEALING OPERATION

In the event a sealing error occurs, an operator may subsequently attempt to seal or reseal the blood vessel using the same routines 200, 212 shown in FIGS. 4 and 5. Such resealing operation occurs while maintaining the jaws 52, 54 at the sealing area.

For various reasons, during a resealing operation a heating stage measured current value that is stored as the $I_{max}$ current value typically does not approach a value remotely close to an $I_{max}$ current value measured during a first sealing attempt. By multiplying the stored $I_{max}$ current value by the predetermined percentage value $\%_{th}$ to determine the boiling of liquid in a blood vessel, the digital processor 110 determines a boiling condition even when the $I_{max}$ current value does not attain a generally expected current value for an initial sealing attempt. Thus, utilizing a predetermined percentage $\%_{th}$ of the $I_{max}$ current value provides proper boiling detection as compared to utilizing a predetermined required current limit value or a voltage limit value that may never be obtained. In the sealing stage routine 212 shown in FIG. 5, the processor 110 determines a completed seal when the decreasing $\Delta I_{calc}$, value is less than a $\Delta I_{shutoff}$ value as discussed above. Thus, no specific large or small $I_{meas}$ current value or $V_{meas}$ voltage value is required to determine completion of the resealing of a blood vessel. Therefore, providing a different routine or algorithm to perform calculations is not necessary to reseal the blood vessel.

ENHANCEMENT RESEALING OPERATION

Figure 10:
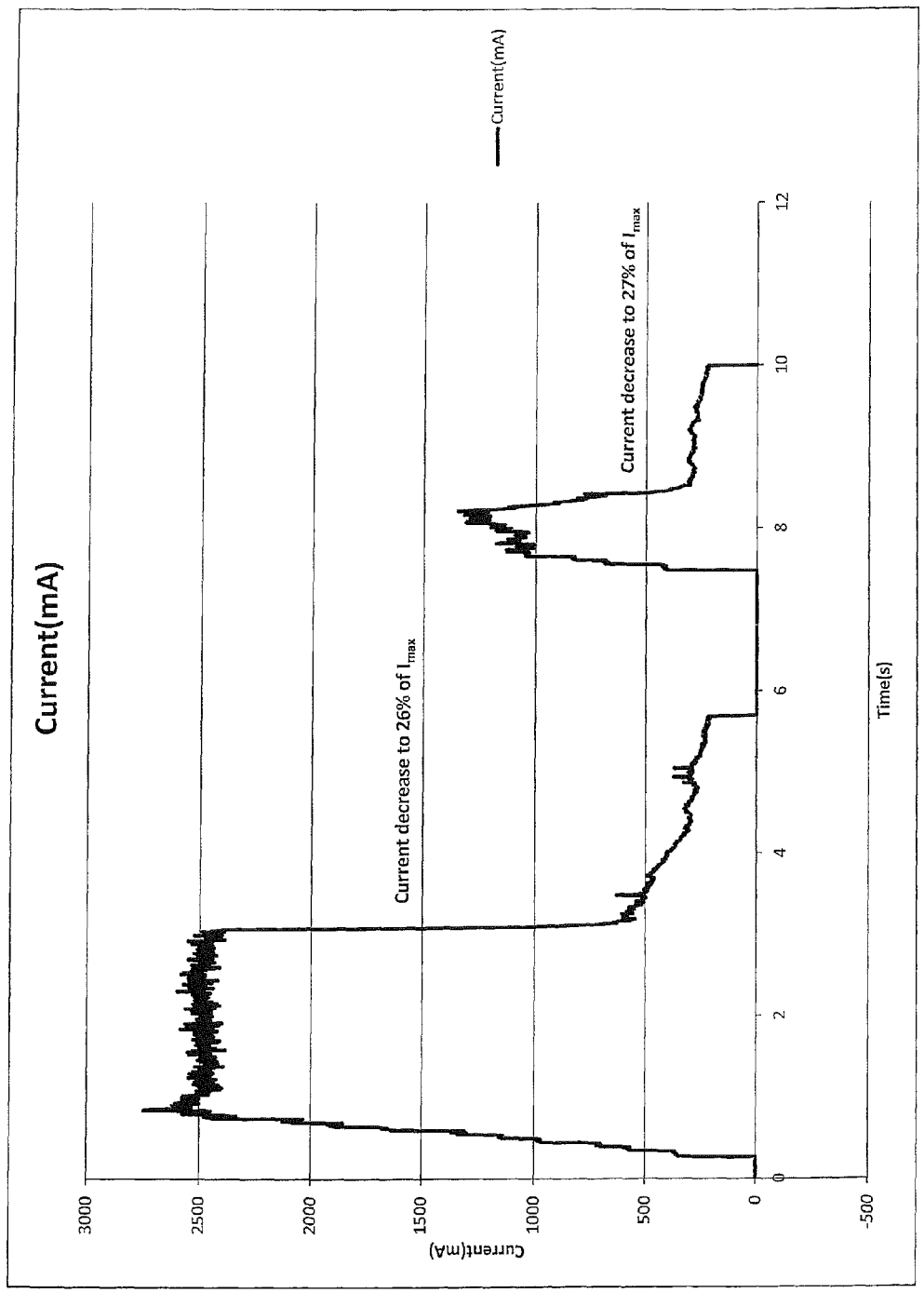
FIG. 10 is a graph displaying measured current for a seal enhancement embodiment of the invention.
Figure 11:
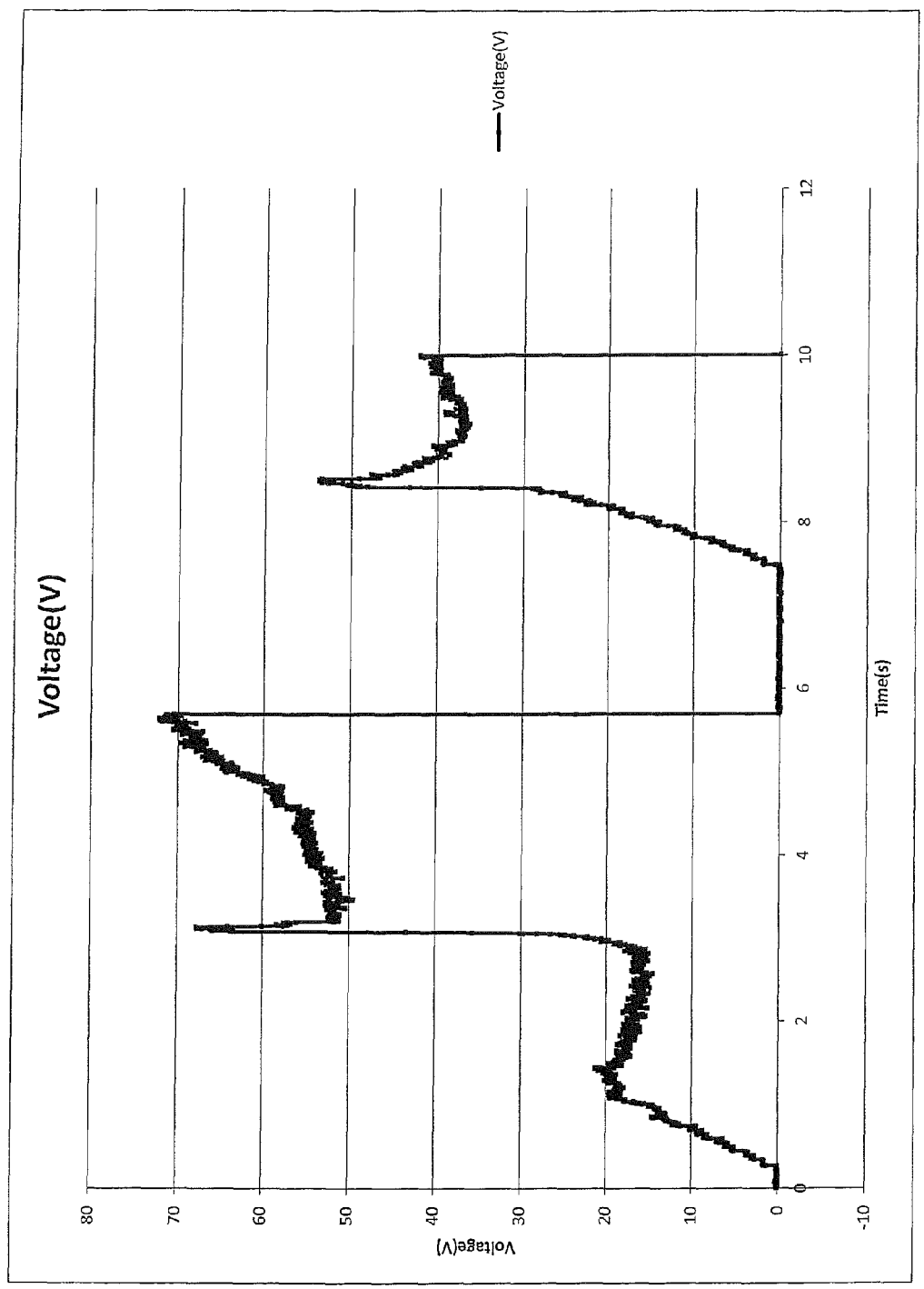
FIG. 11 is a graph displaying measured voltage for the embodiment shown in FIG. 10.

Besides resealing a blood vessel in response to an indication that a sealing operation may be incomplete as disclosed above, many surgical personnel routinely perform a resealing operation to enhance the quality of the seal. Examples of enhancement resealing operations are shown in the graphs of FIGS. 10 and 11, which specifically illustrate an original sealing followed by an enhancement resealing operation. The current measurement graph of FIG. 10 shows a first sealing operation occurring within the first six seconds of time and a second resealing operation is shown on the same graph for purposes of comparison that starts at a time of about 7.5 seconds and ends about 10 seconds after the first previous sealing operation occurred. The graph of the current for the first sealing operation shown in FIG. 10 is the same as the sealing operation for the current as shown in FIG. 7. A gap of more than 1.5 seconds is shown between the first sealing and the second enhancement sealing operation. The time gap is insignificant and simply corresponds to the delay before a user manually begins a second enhancement operation of the RF generator 100.

As in the embodiment disclosed in FIGS. 6-9, and specifically in the graph of current shown in FIG. 7, the measured current as shown in FIG. 10 increases rapidly during voltage ramping of the heating stage and the current value obtains the ramp current limit value of 2,500 mA. Thus, the stored $I_{max}$ current value is 2,500 mA. After about 3 seconds, the $I_{meas}$ current then suddenly decreases to a value of about 600 mA, which is a decrease to about 26% of the $I_{max}$ current value. This sudden decrease to an $I_{meas}$ current value of about 600 mA is much less than a $\%_{th}$ threshold of, for example, 85% of the $I_{max}$ current value of 2,500 mA. The processor 110 then advances the sealing operation from heating stage 1 to sealing stage 2 as a result of the $I_{meas}$ current value being less than 85% of 2,500 mA.

At the second enhancement sealing operation shown in FIG. 10, and during the voltage ramping shown in FIG. 11, there is a similar quick increase in $I_{meas}$ current until a level of about 1,350 mA is obtained. Thus, for the enhancement resealing, the $I_{meas}$ current value does not approach either the ramp current limit value of 2,500 mA or the ramp voltage limit value as in the first sealing operation. As shown in FIG. 10, a sudden decrease in current to a value of about 350 mA occurs, which is a % decrease to about 27% of the $I_{max}$ current value. As the $\%_{th}$ threshold is a single value between about 60% and about 90%, the sealing operation advances to the sealing stage. Thereafter, the sealing stage operates as in the embodiments previously described. Note that the entire enhancement resealing operation shown in FIGS. 10 and 11 requires less than 3 seconds. Thus, the amount of voltage and current output required to enhance the seal for the tissue and blood vessels is not as great as compared to completing an original seal. Therefore, the benefit of relying on the $\%_{th}$ measurement of a decrease in current, rather than $I_{meas}$ current values to control the sealing enhancement operation is clearly observable.

Figure 12:
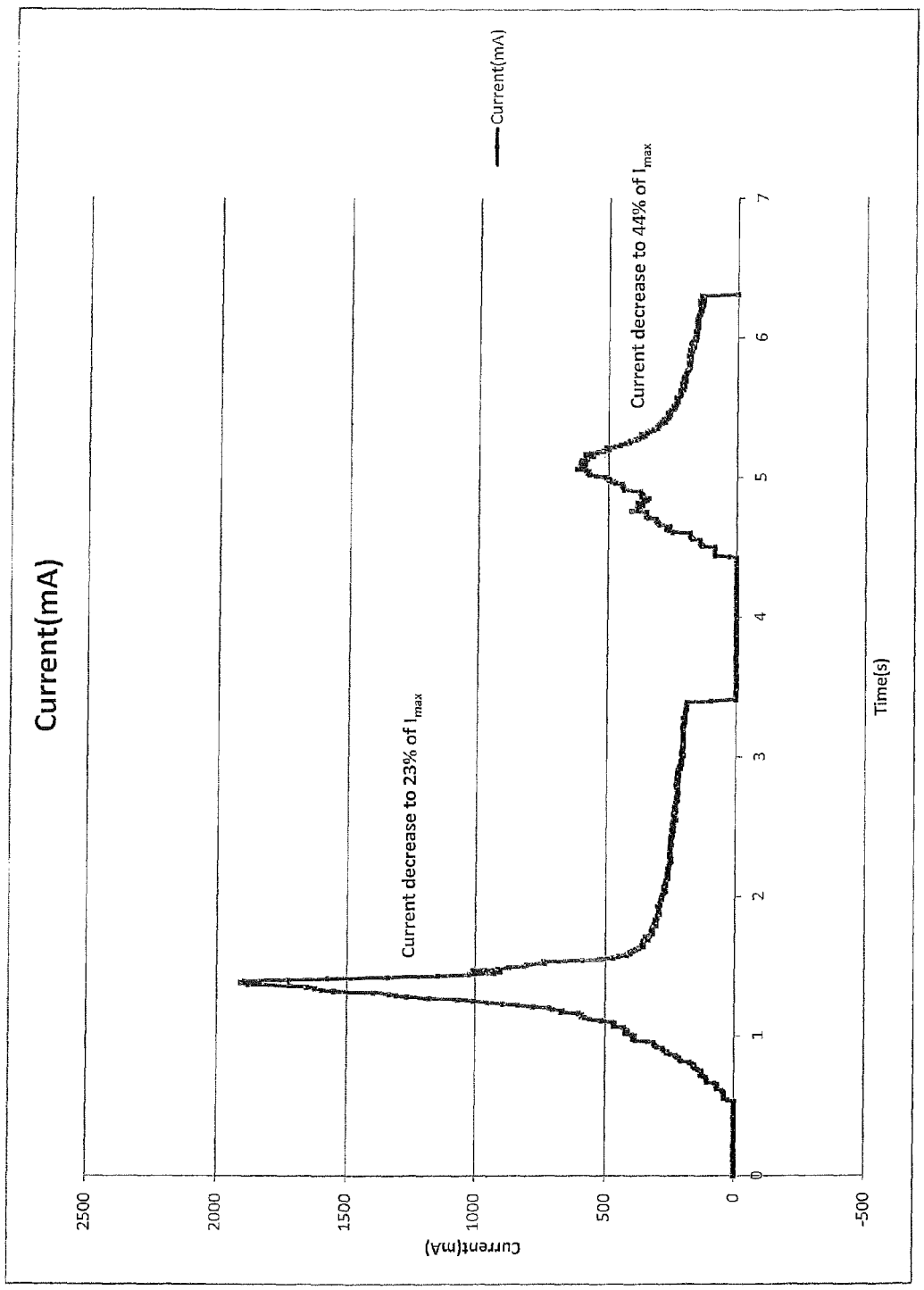
FIG. 12 is a graph showing measured current for a first seal and an enhancement seal of a mesentery tissue.

FIG. 12 shows another current versus time graph for sealing and enhancement sealing of tissue, and specifically application of RF energy to seal mesentery tissue. Actuation of the RF generator 100 begins at about 0.5 seconds on the FIG. 12 graph. Mesentary tissue is typically much stronger and thicker than other tissue. In this use of a RF energy console 10 with a handpiece 40, during the heating stage with voltage ramping occurring, the $I_{meas}$ current value increases in about one second to a $I_{meas}$ value of less than 2,000 mA as shown in FIG. 12. The $I_{meas}$ current value, when boiling of liquid and tissue begins, suddenly decreases to about 23% of the previously stored $I_{max}$ current value of almost 2,000 mA. This value is much less than the single $\%_{th}$ threshold value from 60% to 90% provided to the processor 110 from the handpiece memory 130. As in the earlier embodiments, the processor 110 advances to the sealing stage and operates until stopping about 2.7 to 3.0 seconds after the starting of the sealing operation when a completed seal is indicated.

As shown in FIG. 12, a second enhancement resealing operation begins wherein during the voltage ramping of the heating stage, the $I_{meas}$ current value attains a value of about 600 mA. Thereafter, a decrease to about 44% of the measured and stored $I_{max}$ current value of about 600 mA occurs. Thus, in the FIG. 12 example, the percentage decrease in current is much less than in original initial sealing. Therefore, the approach of measuring percentage current decreases provides better results for the RF energy console.

The RF energy output by the RF generator 100 of the RF energy console 10 is a continuous RF output, and thus is free from RF energy pulses.

The flow charts shown in FIGS. 4 and 5 represent one embodiment of the invention. Other embodiments include additional steps, such as for determining when the sealing operation exceeds an error time limit value. Further, the various steps can be provided in a different order or a single step can be defined as a group of sub-steps.

Although the present invention has been described with respect to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A method of sealing at least one of a blood vessel and tissue by controlling electrosurgical energy provided by an electrosurgical radio frequency (RP) energy console to a handpiece comprising the steps of:
(1) in response to actuation by a user, executing a heating stage, the heating stage including (a) outputting and applying an increasing RF ramping voltage to the handpiece for heating fluid in the at least one of the blood vessel and the tissue; (b) measuring a current ($I_{meas}$) value for the electrosurgical RE energy console; (c) comparing the current ($I_{meas}$) value with a stored maximum current ($I_{max}$) value; (d) updating the stored maximum current ($I_{max}$) value to the current ($I_{meas}$) value and returning to step (b) when the current ($I_{meas}$) value is greater than the stored maximum current ($I_{max}$) value; (e) determining whether the current ($I_{meas}$) value is less than a single predetermined current decrease threshold percentage ($\%_{th}$) value of the stored maximum current ($I_{max}$) value and returning to step (b) when the current ($I_{meas}$) value is greater or equal to the single predetermined current decrease threshold percentage ($\%_{th}$) value of the stored maximum current ($I_{max}$) value; and (f) when the current ($I_{meas}$) value is less than the single predetermined current decrease threshold percentage ($\%_{th}$) value of the stored maximum current ($I_{max}$) value resulting from onset of boiling of the fluid in the at least one of the blood vessel and the tissue, advancing from the heating stage to a sealing stage;
(2) the sealing stage including (a) outputting a sealing voltage from the electrosurgical RF energy console to the handpiece and (b) adjusting the sealing voltage to maintain an increasing essentially constant predetermined change of impedance ($\Delta Z_{seal}$) value.

2. The method according to claim 1, wherein the step of (2)(b) adjusting the sealing voltage that is output from the electrosurgical RF energy console to maintain the increasing essentially constant predetermined change of impedance ($\Delta Z_{seal}$) value comprises the steps of:
(i) measuring a voltage ($V_{meas}$) value and the current ($I_{meas}$) value of energy output by the electrosurgical RF energy console a plurality of times to thereby measure a plurality of voltage ($V_{meas}$) values and a plurality of current ($I_{meas}$) values;
(ii) storing the plurality of the voltage ($V_{meas}$) values and the plurality of current ($I_{meas}$) values;
(iii) calculating a change of current ($\Delta I_{calc}$) value essentially from the plurality of current ($I_{meas}$) values stored in step (2)(b)(ii);
(iv) calculating a change of impedance ($\Delta Z_{calc}$) value essentially from the plurality of voltage ($V_{meas}$) values stored in step (2) (b) (ii) and the plurality of current ($I_{meas}$) values stored in step (2)(b)(ii);
(v) adjusting the sealing voltage that is output by the electrosurgical RF energy console so that the change of impedance ($\Delta Z_{calc}$) value essentially equals the increasing essentially constant predetermined change of impedance ($\Delta Z_{seal}$) value;
(vi) determining to return and returning to step (i) when an absolute value of the change of current ($\Delta I_{calc}$) value is essentially greater than an absolute value of a predetermined change of current ($\Delta I_{shutoff}$) value; and
(vii) stopping the sealing voltage that is output from the electrosurgical RF energy console to power the handpiece when the absolute value of the change of current ($\Delta I_{calc}$) value is essentially less than the absolute value of the predetermined change of current ($\Delta I_{shutoff}$) value.

3. The method according to claim 2, wherein the predetermined change of current ($\Delta I_{shutoff}$) value comprises a single value between about −20 mA/second and about −80 mA/second, and wherein the single predetermined current decrease threshold percentage ($\%_{th}$) value of the stored maximum current ($I_{max}$) value is between about 40% and about 90%.

4. The method according to claim 2, including the electrosurgical RF energy console reading the predetermined change of current ($\Delta I_{shutoff}$) value for the sealing stage from a handpiece memory that is provided with a cable of the handpiece, the method including the step of, during the sealing stage, stopping output of the sealing voltage from the electrosurgical RF energy console when the absolute value of the change of current ($\Delta I_{calc}$) value is less than the absolute value of the predetermined change of current ($\Delta I_{shutoff}$) value before a predetermined sealing error time limit expires.

5. The method according to claim 4, including the following steps carried out by the electrosurgical RF energy console:
reading the increasing RF ramping voltage and a predetermined current limit value from the handpiece memory; and
reading the single predetermined current decrease threshold percentage ($\%_{th}$) value of the stored maximum current ($I_{max}$) value from the handpiece memory.

6. The method according to claim 2, further comprising the steps of:
during the heating stage, stopping the increasing RF ramping voltage output from the electrosurgical RF energy console after a predetermined heating error time limit when the current ($I_{meas}$) value is not determined to be less than the single predetermined current threshold percentage ($\%_{th}$) value of the stored maximum current ($I_{max}$) value before the predetermined heating error time limit expires; and
during the sealing stage, stopping the sealing voltage output from the electrosurgical RF energy console when the absolute value of the change of current ($\Delta I_{calc}$) value is less than the absolute value of the predetermined change of current ($\Delta I_{shutoff}$) value before the predetermined heating error time limit expires.

7. The method according to claim 2, including the step of resealing the at least one of the blood vessel and the tissue by repeating the steps (1)(a)-(f) and (2)(a)-(b)(i)-(vii) in response to a reseal activation by the user of the electrosurgical RE energy console, wherein the resealing activation operates in the same manner as the sealing stage.

8. The method of claim 2, wherein the predetermined change of current ($\Delta I_{shutoff}$) value during the sealing stage comprises a single value between about −20 mA/second and about −80 mA/second.

9. The method according to claim 1, including the step of identifying the handpiece connected to the electrosurgical RF energy console and providing the increasing RF ramping voltage as a predetermined start-up increasing voltage ramping value corresponding to the handpiece and providing the single predetermined current threshold percentage ($\%_{th}$) value of the stored maximum current ($I_{max}$) value that is between 40% and 90% as a percentage value corresponding to the handpiece.

10. The method according to claim 1, including comparing the current ($I_{meas}$) value with a predetermined stored current limit value and limiting current that is output by the electrosurgical RF energy console when the current ($I_{meas}$) value essentially equals the predetermined stored current limit value.

11. The method according to claim 1, wherein the heating stage includes the step of discontinuing output of the increasing RF ramping voltage from the electrosurgical RF energy console after a predetermined heating error time limit when the current ($I_{meas}$) value is not less than the single predetermined current decrease threshold percentage ($\%_{th}$) value of the stored maximum current ($I_{max}$) value before the predetermined heating error time limit expires.

12. The method according to claim 11, including the step of reading the predetermined heating error time limit from a handpiece memory.

13. The method according to claim 1, wherein the single predetermined current decrease threshold percentage ($\%_{th}$) value of the stored maximum current ($I_{max}$) value is between 70% and 90%, and wherein the increasing RF ramping voltage and the sealing voltage output from the electrosurgical RE energy console results in essentially continuous RF energy free from RF pulses.

14. The method according to claim 1, further including:
providing a closing force to the at least one of the blood vessel and the tissue with first and second jaws of the handpiece;
applying sealing RF energy during the sealing stage to the at least one of the blood vessel and the tissue with the first jaw;
providing a return path with the second jaw;
connecting the electrosurgical RF energy console by a cable to the handpiece; and
providing the electrosurgical RF energy console with:
a sensor apparatus measuring a voltage value of the sealing voltage and the current ($I_{meas}$) value;
a processor receiving the voltage value and the current ($I_{meas}$) value from the sensor apparatus, the processor calculating at least one of a change in current and a change in impedance from the voltage value and the current ($I_{meas}$) value, the processor operating as a feedback circuit and providing a signal output; and
a controller feedback circuit receiving the signal output from the processor and receiving at least one of the voltage value and the current ($I_{meas}$) value from the sensor apparatus, the controller feedback circuit providing an output signal that controls the electrosurgical RF energy console in response to the signal output of the processor and the at least one of the voltage value and the current ($I_{meas}$) value received from the sensor apparatus.

15. The method of claim 14, wherein the controller feedback circuit comprises an analog controller feedback circuit and wherein the sensor apparatus comprises an analog sensor apparatus, and the analog sensor apparatus providing each of the voltage value and the current ($I_{meas}$) value to each of the processor and the analog controller feedback circuit.

16. The method of claim 14, wherein the processor receives each of the voltage value and the current ($I_{meas}$) value from the sensor apparatus, the processor calculating and providing the output signal to the controller feedback circuit to control the electrosurgical RF energy console to output the RF ramping voltage during the heating stage, the processor providing the signal output to prevent the electrosurgical RF energy console from outputting the current ($I_{meas}$) value beyond the stored maximum ($I_{max}$) current value when the stored maximum ($I_{max}$) current value is reached during the heating stage before the processor determines the single predetermined decrease threshold percentage ($\%_{th}$) value of the stored maximum ($I_{max}$) current value in the current ($I_{meas}$) value for advancement to the sealing stage.

17. The method of claim 16, wherein the single predetermined current decrease threshold percentage ($\%_{th}$) value of the stored maximum ($I_{max}$) current value is a single percentage value that is between about 60% and about 90%, the stored maximum ($I_{max}$) current value is between about 1000 mA and about 5000 mA, and wherein the increasing RF ramping voltage and the sealing voltage output from the electrosurgical RF energy console results in essentially continuous RF energy free from RF pulses.

18. The method of claim 16, wherein the handpiece includes a handpiece memory for storing a ramping voltage value of the increasing RF ramping voltage, the increasing essentially constant predetermined change of impedance ($\Delta Z_{seal}$) value, the predetermined change of current ($\Delta I_{shutoff}$) value, a predetermined heating error time limit value, and a predetermined sealing error time limit value, and wherein the processor reads the increasing RF ramping voltage value, the increasing essentially constant predetermined change of impedance ($\Delta Z_{seal}$) value, the predetermined change of current ($\Delta I_{shutoff}$) value, the predetermined heating error time limit value, and the predetermined sealing error time limit value from the handpiece memory.

19. The method of claim 16, wherein the electrosurgical RF energy console enhances a seal of the at least one of the blood vessel and the tissue by a repeat application of the increasing RF ramping voltage to the handpiece, and during the sealing stage, storing of the current ($I_{meas}$) value and storing of the voltage value for calculating a change in actual impedance value and a change in actual current value output by the electrosurgical RF energy console, the processor comparing the change in actual impedance value and the increasing essentially constant predetermined change of impedance ($\Delta Z_{seal}$) value for providing the signal output to the controller feedback circuit to maintain the change in actual impedance value at the increasing essentially constant predetermined change of impedance ($\Delta Z_{seal}$) value until an absolute value of the change in actual current value is less than an absolute value of the increasing essentially constant predetermined change of impedance ($\Delta Z_{seal}$) value, whereby the output of RF energy from the electrosurgical RF energy console is terminated, and executing an enhancement resealing operation comprising the steps (a) outputting an enhancement resealing voltage from the electrosurgical RF energy console to the handpiece and (b) adjusting the enhancement resealing voltage to maintain a second increasing essentially constant predetermined change of impedance ($\Delta Z_{2seal}$) value.

20. The method of claim 14, wherein during the heating stage, the processor determines a percentage value decrease in the current ($I_{meas}$) value by storing the stored maximum current ($I_{max}$) value during the heating stage, and when a subsequent measured current value is less than a predetermined percentage value of the stored maximum current ($I_{max}$) value, the processor advances to the sealing stage.

21. The method of claim 20, wherein during the heating stage, the processor discontinues output of the increasing RF ramping voltage from the electrosurgical RF energy console when the processor does not advance to the sealing stage before a predetermined heating error time limit expires, and wherein during the sealing stage the processor discontinues output of the sealing voltage when the electrosurgical RF energy console does not complete the sealing stage before a predetermined sealing error time limit expires.

22. The method of claim 14, wherein the handpiece includes a handpiece memory for storing a value of the increasing RF ramping voltage, the increasing essentially constant predetermined change of impedance ($\Delta Z_{seal}$) value and the predetermined change of current ($\Delta I_{shutoff}$) value, and wherein the processor reads the increasing RF ramping voltage value, the increasing essentially constant predetermined change of impedance ($\Delta Z_{seal}$) value, the predetermined change of current ($\Delta I_{shutoff}$) value, the predetermined heating error time limit value, and the predetermined sealing error time limit value from the handpiece memory.

* * * * *

UNITED STATES PATENT AND TRADEMARK OFFICE
CERTIFICATE OF CORRECTION

PATENT NO. : 9,161,813 B2  Page 1 of 1
APPLICATION NO. : 13/911673
DATED : October 20, 2015
INVENTOR(S) : Steffan Benamou It is certified that error appears in the above-identified patent and that said Letters Patent is hereby corrected as shown below:

In the claims

Column 11, line 30; change "(RP) energy console" to ---(RF) energy console---

Column 11, line 37; change "RE energy console" to ---RF energy console---

Column 13, line 5; change "RE energy console" to ---RF energy console---

Column 13, line 41; change "RE energy" to ---RF energy---

Signed and Sealed this
Fifth Day of April, 2016

Michelle K. Lee
*Director of the United States Patent and Trademark Office*